United States Patent
Arakawa et al.

(10) Patent No.: US 8,362,052 B2
(45) Date of Patent: Jan. 29, 2013

(54) ISOINDOLIN-1-ONE DERIVATIVE

(75) Inventors: Keisuke Arakawa, Tsukuba (JP); Teruyuki Nishimura, Gotenba (JP); Yuichi Sugimoto, Kobe (JP); Hiroyuki Takahashi, Tsukuba (JP); Tadashi Shimamura, Tsukuba (JP)

(73) Assignee: MSD K.K., Tokyo (JP)

( * ) Notice: Subject to any disclaimer, the term of this patent is extended or adjusted under 35 U.S.C. 154(b) by 0 days.

(21) Appl. No.: 13/203,843

(22) PCT Filed: Mar. 9, 2010

(86) PCT No.: PCT/JP2010/054288
§ 371 (c)(1),
(2), (4) Date: Aug. 30, 2011

(87) PCT Pub. No.: WO2010/104195
PCT Pub. Date: Sep. 16, 2010

(65) Prior Publication Data
US 2011/0312976 A1  Dec. 22, 2011

(30) Foreign Application Priority Data
Mar. 11, 2009  (JP) .................... 2009-058281

(51) Int. Cl.
*A01N 43/80* (2006.01)
*A61K 31/425* (2006.01)
*C07D 275/02* (2006.01)

(52) U.S. Cl. ................... 514/372; 548/206
(58) Field of Classification Search .......... 514/372; 548/206
See application file for complete search history.

(56) References Cited

U.S. PATENT DOCUMENTS

| | | | |
|---|---|---|---|
| 4,964,895 A | 10/1990 | Moedritzer et al. | |
| 2008/0108659 A1 | 5/2008 | Gandhi et al. | |
| 2010/0274022 A1 | 10/2010 | Tsujimoto et al. | |
| 2011/0065739 A1 | 3/2011 | Ishikawa et al. | |

FOREIGN PATENT DOCUMENTS

| WO | 98/42666 A1 | 10/1998 |
|---|---|---|
| WO | 02/081447 A1 | 10/2002 |
| WO | 2005/037789 A1 | 4/2005 |
| WO | 2007/021308 A1 | 2/2007 |
| WO | 2008/139879 A1 | 11/2008 |
| WO | 2009/147990 A1 | 12/2009 |

OTHER PUBLICATIONS

A. Hirasawa, et al., "Free Fatty acids regulate gut incretin glucagon-like peptide-1 secretion through GPR120", Nature Medicine, vol. 11, No. 1, pp. 90-94 (2005).
Written Opinion of the International Search Report for U.S. Appl. No. 13/203,843.
PCT International Preliminary Report on Patentabililty for U.S. Appl. No. 13/203,843.
A. Abou-Ouf et et., "1. Synthesis and characterization of some substitutued aminocresols structurally related to certain antimalarials", Egyptian Journal of Pharmaceutical Sciences, vol. 21, No. 21, 177 (1982)—abstract.

*Primary Examiner* — Paul V. Ward
(74) *Attorney, Agent, or Firm* — Kenrick L. Vidale; John C. Todaro

(57) ABSTRACT

The present invention relates to a compound represented by formula (I): (wherein R, $R^2$, $R^3$ and $R^4$ each independently represent a hydrogen or halogen atom; $R^5$ and $R^6$ each independently represent a hydrogen atom or lower alkyl or together represent oxo; X represents C(O) or the like; Y represents an oxygen atom or the like; Z represents a hydrogen atom or the like; R represents 5- or 6-membered heteroaryl having 1-3 hetero atoms selected from the group consisting of nitrogen, sulfur and oxygen atoms, contained within a ring, or the like) or to a pharmaceutically acceptable salt thereof.

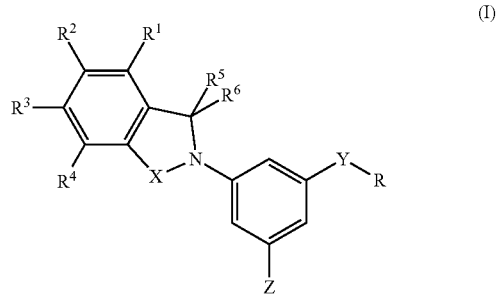

(I)

11 Claims, No Drawings

ISOINDOLIN-1-ONE DERIVATIVE

CROSS-REFERENCE TO RELATED APPLICATIONS

This application is a U.S. National Phase application under 35 U.S.C. §371 of PCT Application Ser. PCT/JP2010/054288, filed Mar. 9, 2010, which claims priority under 35 U.S.C. §119 to Japanese Application No. 2009-058281, filed Mar. 11, 2009.

TECHNICAL FIELD

The present invention relates to isoindolin-1-one derivatives that are useful in the pharmaceutical field. The compounds act as GPR120 receptor (14273) function regulating agents (modulators), which are useful as drugs for treating and/or preventing diabetes, obesity and hyperlipidemia.

BACKGROUND ART

GPR120, a G protein-coupled receptor, causes intracellular signaling through binding with unsaturated long chain fatty acid, such as alpha-linoleic acid, to induce various biological reactions. Actions of GPR120 and its ligand have been reported to promote secretion of GLP-1 (glucagon-like-peptide-1) having the function of reducing a blood glucose level in the gastrointestinal cell lines. (see Nature Medicine, vol. 11, No. 1, January 2005, pp. 90-94). GLP-1, which is a peptide hormone released from L cells which are enteroendocrine cells present in the ileum, the large intestine and the like, has been found to induce insulin secretion depending on a blood glucose level. Accordingly, compounds having the action of promoting GLP-1 secretion are expected as agents for treating diabetes mellitus that allow avoidance of the risk of hypoglycemia due to drug overdosage. GLP-1 is also suggested to be efficacious for delaying the apoptosis of beta cells in type II diabetes mellitus or prolonging the efficacy of islet cell transplantation against type I diabetes mellitus because of having the action of inducing pancreatic beta-cell growth and differentiation from stem cells. GPR120 is known to be also expressed in adipocytes. GPR120 has been found to be increasingly expressed by adipose differentiation induction. In addition, actions of GPR120 and its ligand have been reported to suppress lipolysis in adipose-differentiated cells. A high blood lipid level is known to be one of the causes of insulin resistance. Suppression of lipolysis by a GPR120 agonist is thus expected to decrease the level of free fatty acid in blood to normalize a blood lipid level, resulting in improvement in insulin resistance. Furthermore, GPR120 is also expressed in the pituitary gland, and a GPR120 ligand is reported to suppress adrenocorticotropic hormone secretion. Adrenocorticotropic hormone promotes glucocorticoid secretion downstream thereof to induce action such as promotion of glyconeogenesis in the liver, inhibitory action against glucose uptake in muscle and peripheral tissue, lipolysis in adipose tissue or release of fatty acid or glycerol. Accordingly, GPR120 is considered to exhibit hypoglycemic action or blood lipid lowering action via suppression action against adrenocorticotropic hormone secretion even in the center. In light of the above description, a compound having GPR120 agonist activity is considered to be extremely useful as an agent for treating and/or preventing diabetes mellitus, obesity and hyperlipidemia.

Compounds related structurally to a compound according to an embodiment of the present invention include, e.g., a compound represented by the following formula:

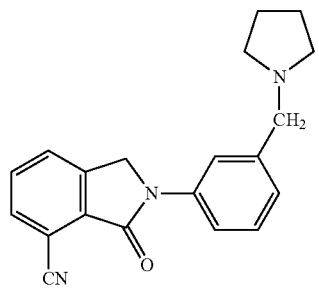 [SMILES: N#Cc1cccc2c1C(=O)N(c1cccc(CN3CCCC3)c1)C2]

which is described (see US 20080108659). The compound in accordance with US 20080108659 has cyano on the benzene ring of isoindolin-1-one, whereas a compound according to an embodiment of the present invention has no cyano group. In addition, the compound according to an embodiment of the present invention always has oxo on cycloalkyl, which is composed of carbon atoms of which one may be substituted with a nitrogen atom, whereas the compound in accordance with US 20080108659 has no oxo group. Furthermore, use of the compound according to US 20080108659 is treatment of cancer, but it is not disclosed or suggested that the compound according to US 20080108659 is useful in treatment and/or prevention of diabetes, obesity and hyperlipidemia.

A compound represented by the following formula:

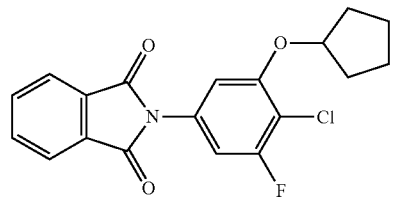 [SMILES: O=C1c2ccccc2C(=O)N1c1cc(F)c(Cl)c(OC2CCCC2)c1]

is also described (see WO 2005037789). Although the compound has a phthalimide backbone, cyclohexyl in the compound has no oxo group whereas cycloalkyl in a compound according to an embodiment of the present invention always has oxo. In addition, the compound according to WO 2005037789 is used for a herbicide, but it is not disclosed or suggested that the compound according to WO 2005037789 is useful in treatment and/or prevention of diabetes, obesity and hyperlipidemia.

Compounds having isoindolin-1-one skeleton are described in WO 2002081447 and WO 199842666. In the compounds, cycloalkyl has no oxo group. A substituent on a benzene ring constituting isoindolin-1-one skeleton is different from that of the compound according to an embodiment of the present invention. In addition, use in accordance with WO 2002081447 and WO 199842666 relates to inflammatory diseases/autoimmune diseases, but WO 2002081447 and WO 199842666 do not disclose or suggest that the compounds are useful in treatment and/or prevention of diabetes, obesity and hyperlipidemia.

A compound represented by the following formula:

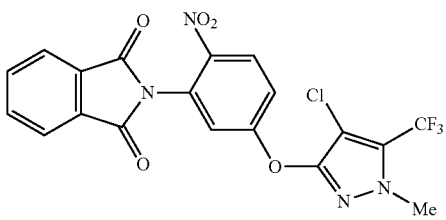 [SMILES: Cn1nc(Oc2ccc([N+](=O)[O-])c(N3C(=O)c4ccccc4C3=O)c2)c(Cl)c1C(F)(F)F]

or the like is also described (see U.S. Pat. No. 4,964,895). The compound according to U.S. Pat. No. 4,964,895 inevitably contains a nitro group in a para position of a phenyl group constituting phenoxypyrazole whereas a compound according to an embodiment of the present invention has no nitro group. In addition, the compound is used for a herbicide, but it is not disclosed or suggested that the compound is useful in treatment and/or prevention of diabetes, obesity and hyperlipidemia.

A compound represented by the following formula:

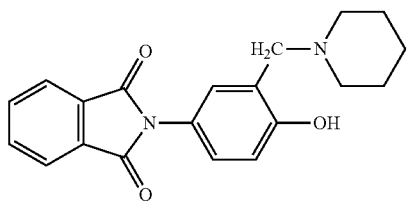 [SMILES: O=C1c2ccccc2C(=O)N1c1ccc(O)c(CN2CCCCC2)c1]

or the like is also described (see Egyptian Journal of Pharmaceutical Sciences, vol. 21, pp. 177-187, 1982). From such compounds, containing piperidinyl having no oxo group, a compound according to an embodiment of the present invention differs in its inevitably having an oxo group in case of containing cycloalkyl, piperidinyl, etc. In addition, such compounds always have a hydroxy group on a phenyl group whereas the compound according to an embodiment of the present invention has no hydroxy group on a phenyl group bound to a nitrogen atom of a phthalimido group. Furthermore, the document, Egyptian Journal of Pharmaceutical Sciences, vol. 21, pp. 177-187, 1982, describes that the compound according thereto is useful as an antimalarial drug, but does not disclose or suggest that the compound is useful in treatment and/or prevention of diabetes, obesity and hyperlipidemia.

DISCLOSURE OF THE INVENTION

It is desirable to provide a novel isoindolin-1-one derivative having a GPR120 (14273) agonist action.

We, the present inventors have assiduously studied to develop a compound having a GPR120 (14273) function regulating action, particularly having an agonist action, and found that the compound according to an embodiment of the present invention is efficacious as the compound having the GPR120 (14273) function regulating action, and the invention was thus accomplished based on such findings.

Specifically, the present invention relates to a compound represented by a formula (I):

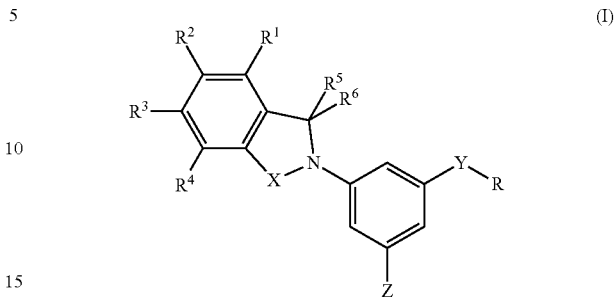

or a pharmaceutically acceptable salt thereof, wherein:
$R^1$, $R^2$, $R^3$ and $R^4$ each independently represent a hydrogen or halogen atom;
$R^5$ and $R^6$ each independently represent a hydrogen atom or lower alkyl or together represent oxo;
X represents C(O) or $S(O)_2$;
Y represents an oxygen or sulfur atom, NH or $CH_2$;
Z represents a hydrogen or halogen atom;
R represents
(1) 5- or 6-membered heteroaryl having 1-3 hetero atoms selected from the group consisting of nitrogen, sulfur and oxygen atoms, contained within a ring,
said 5- or 6-membered heteroaryl is optionally substituted with 1 to 3 same or different lower alkyl, lower alkoxy or halogen atoms,
said lower alkyl and lower alkoxy is optionally substituted with 1 to 3 same or different halogen atoms, or
(2) $C_{3-7}$ cycloalkyl substituted with oxo,
one of carbon atoms of said $C_{3-7}$ cycloalkyl is optionally replaced by nitrogen atom, and
said $C_{3-7}$ cycloalkyl in which one carbon atom is replaced by nitrogen atom is optionally substituted with 1 to 3, same or different lower alkyl, lower alkoxy or halogen atoms,
said lower alkyl and lower alkoxy is optionally substituted with 1 to 3 same or different halogen atoms.

The present invention also relates to a GPR120 function regulating agent containing a compound represented by the formula (I) or a pharmaceutically acceptable salt thereof as an active ingredient. Particularly, the present invention relates to a GPR120 (14273) agonist containing a compound represented by the formula (I) or a pharmaceutically acceptable salt thereof as an active ingredient.

The present invention also relates to an agent for treating and/or preventing diabetes, obesity or hyperlipidemia, containing a compound represented by the formula (I) or the pharmaceutically acceptable salt thereof, as an active ingredient.

Furthermore, the present invention relates to a pharmaceutical composition containing the compound represented by the formula (I) and the pharmaceutically acceptable carrier.

A compound (I) according to an embodiment of the present invention or the pharmaceutically acceptable salt thereof has a strong GPR120 (14273) function regulating action, particularly an agonist action, and is useful for treating and/or preventing diabetes, obesity or hyperlipidemia.

The meanings of terms as used herein are described below, and a compound according to an embodiment of the present invention is described in further detail.

The term "halogen atom" includes, for example, fluorine, chlorine, bromine and iodine atoms.

The term "lower alkyl" means linear or branched $C_{1-6}$ alkyl, of which examples include methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl and 1-ethyl-2-methylpropyl.

The term "lower alkoxy" means a group, in which a hydrogen atom of hydroxy is substituted with the above-mentioned lower alkyl, and of which examples include methoxy, ethoxy, propoxy, isopropoxy, butoxy, sec-butoxy, tert-butoxy, pentyloxy, isopentyloxy, hexyloxy and isohexyloxy.

The term "$C_{3-7}$ cycloalkyl" means a cycloalkyl group having 3 to 7 carbon atoms, specifically includes, for examples, cyclopropyl, cyclobutyl, cyclopentyl, cyclohexyl and cycloheptyl.

Each symbol used in the formula (I) in accordance with an embodiment of the present invention

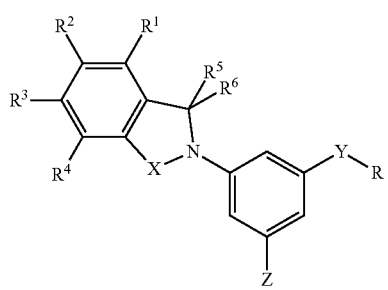

(I)

is specifically described.

$R^1$, $R^2$, $R^3$ and $R^4$ each independently represent a hydrogen or halogen atom.

"Halogen atom" represented by $R^1$, $R^2$, $R^3$ and $R^4$ includes identical groups as the halogen atoms defined above, of which examples specifically include fluorine, chlorine, bromine and iodine atoms.

$R^5$ and $R^6$ each independently represent a hydrogen atom or lower alkyl or together represent oxo.

"Lower alkyl" represented each independently by $R^5$ and $R^6$ is identical as the lower alkyl defined above, of which examples specifically include methyl, ethyl, propyl and isopropyl.

X represents C(O) or S(O)$_2$;

Y represents an oxygen or sulfur atom, NH or CH$_2$.

Among these, Y is preferably an oxygen atom or CH$_2$, more preferably an oxygen atom.

Z represents a hydrogen or halogen atom.

"Halogen atom" represented by Z are identical groups as the halogen atoms defined above, of which examples specifically include fluorine, chlorine, bromine and iodine atoms.

R represents
(1) 5- or 6-membered heteroaryl having 1-3 hetero atoms selected from the group consisting of nitrogen, sulfur and oxygen atoms, contained within a ring,
said 5- or 6-membered heteroaryl is optionally substituted with 1 to 3 same or different lower alkyl, lower alkoxy or halogen atoms,
said lower alkyl and lower alkoxy is optionally substituted with 1 to 3 same or different halogen atoms, or
(2) $C_{3-7}$ cycloalkyl substituted with oxo,
one of carbon atoms of said $C_{3-7}$ cycloalkyl is optionally replaced by nitrogen atom, and
said $C_{3-7}$ cycloalkyl in which one carbon atom is replaced by nitrogen atom is optionally substituted with 1 to 3, same or different lower alkyl, lower alkoxy or halogen atoms,
said lower alkyl and lower alkoxy is optionally substituted with 1 to 3 same or different halogen atoms.

Said "5- or 6-membered heteroaryl having 1-3 hetero atoms selected from the group consisting of nitrogen, sulfur and oxygen atoms, contained within a ring" represented by R, includes for example a group selected from the group consisting of pyridinyl, pyrazinyl, pyrimidinyl, pyridazinyl, thiazolyl, thiadiazolyl, oxazolyl and pyrazolyl.

Said 5- or 6-membered heteroaryl is optionally substituted with 1 to 3 same or different lower alkyl, lower alkoxy or halogen atoms.

Lower alkyl of the substituent includes identical groups as the lower alkyl defined above, of which examples specifically include methyl, ethyl, propyl and isopropyl.

The lower alkyl is optionally also substituted with 1 to 3 same or different halogen atoms.

Lower alkoxy of the substituent includes identical groups as the lower alkoxy defined above, of which examples specifically include methoxy, ethoxy, propoxy and isopropoxy.

The lower alkyl and the lower alkoxy is optionally substituted with 1 to 3 same or different halogen atoms defined above.

A halogen atom of the substituent encompasses identical groups as the halogen atoms defined above, of which examples specifically include fluorine, chlorine, bromine and iodine atoms.

As "5- or 6-membered heteroaryl having 1-3 hetero atoms selected from the group consisting of nitrogen, sulfur and oxygen atoms, contained within a ring, which 5- or 6-membered heteroaryl is optionally substituted with 1 to 3 same or different lower alkyl, lower alkoxy or halogen atoms, which lower alkyl and lower alkoxy is optionally substituted with 1 to 3 same or different halogen atoms" represented by R, a group selected from the group consisting of pyridinyl, pyrazinyl, pyrimidinyl, pyridazinyl, thiazolyl, oxazolyl and pyrazolyl is preferred.

The term "$C_{3-7}$ cycloalkyl substituted with oxo" represented by R referring to a group in which the above-defined $C_{3-7}$ cyclopropyl group is substituted with oxo, specifically includes, for example oxocyclopropyl, 2-oxocyclobutyl, 3-oxocyclobutyl, 2-oxocyclopentyl, 3-oxocyclopentyl, 2-oxocyclohexyl, 3-oxocyclohexyl, 4-oxocyclohexyl, 2-cycloheptyl, 3-cycloheptyl and 4-cycloheptyl.

In the $C_{3-7}$ cycloalkyl substituted with oxo, any one carbon atom constituting a $C_{3-7}$ cycloalkyl group is also optionally substituted with a nitrogen atom.

The term "$C_{3-7}$ cycloalkyl substituted with oxo, which $C_{3-7}$ cycloalkyl is composed of carbon atoms, of which one is substituted with a nitrogen atom" specifically includes, for example a group represented by

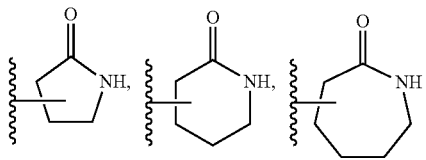

wherein

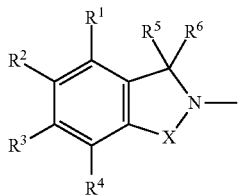

represents a binding site with Y.

"$C_{3-7}$ cycloalkyl substituted with oxo" or "$C_{3-7}$ cycloalkyl substituted with oxo, which $C_{3-7}$ cycloalkyl is composed of carbon atoms, of which one is substituted with a nitrogen atom" may be also substituted with 1 to 3 same or different lower alkyl, lower alkoxy or halogen atoms.

Lower alkyl of the substituent means identical groups as the lower alkyl defined above, of which examples specifically include methyl, ethyl, propyl and isopropyl.

Lower alkoxy of the substituent means identical groups as the lower alkoxy defined above, of which examples specifically include methoxy, ethoxy, propoxy and isopropoxy.

A halogen atom as the substituent means identical atoms as the halogen atoms defined above, of which examples specifically include fluorine, chlorine, bromine and iodine atoms.

The lower alkyl and the lower alkoxy is optionally substituted with 1 to 3 same or different halogen atoms.

Lower alkyl groups substituted with 1 to 3 same or different halogen atoms include, for example fluoromethyl, difluoromethyl and trifluoromethyl.

Lower alkoxy substituted with 1 to 3 same or different halogen atoms include, for example fluoromethoxy, difluoromethoxy and trifluoromethoxy.

As a group represented by a formula (II):

(II)

(wherein each symbol has the same definition specified above) in the formula (I), a group selected from the group consisting of the formula (II-1):

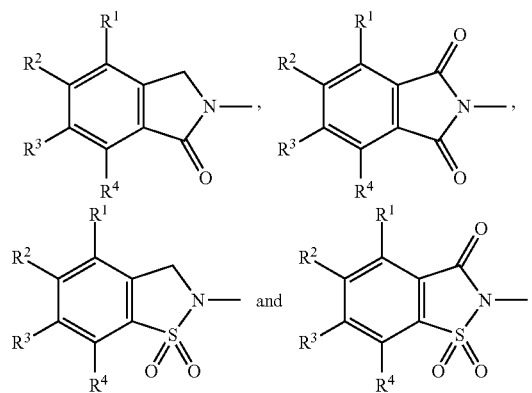

(II-1)

is preferred, and a group selected from the group consisting of the formula (II-2):

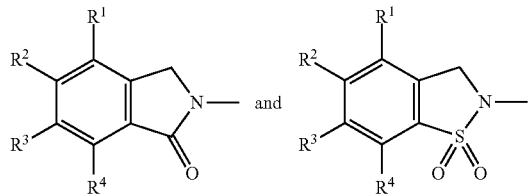

(II-2)

is more preferred.

Compounds according to the embodiment of the present invention represented by the formula (I) include, for example but are not limited to, 2-[3-fluoro-5-(pyridine-3-yloxy)phenyl]isoindolin-1-one, 2-[3-fluoro-5-(pyridine-3-yloxy)phenyl]-2,3-dihydro-1,2-benzisothiazol-1,1-dioxide, 2-[3-fluoro-5-(pyridine-3-yloxy)phenyl]-1H-isoindol-1,3(2H)-dione, 2-[3-fluoro-5-(pyrazin-2-yloxy)phenyl]-2,3-dihydro-1,2-benzisothiazol-1,1-dioxide, 4-fluoro-2-[3-fluoro-5-(pyridine-3-yloxy)phenyl]-1H-1,3(2H)-dione, 7-fluoro-2-[3-fluoro-5-(pyridine-3-yloxy)phenyl]isoindolin-1-one, 4-fluoro-2-[3-fluoro-5-(pyridine-3-yloxy)phenyl]isoindolin-1-one, 5-fluoro-2-[3-fluoro-5-(pyridine-3-yloxy)phenyl]isoindolin-1-one, 2-[3-fluoro-(pyridine-3-yloxy)phenyl]-1,2-benzisothiazol-3(2H)-on-1,1-dioxide, 2-{3-fluoro-5-[(6-methylpyridine-3-yl)oxy]phenyl}isoindolin-1-one, 2-{3-fluoro-5-[(3-methylpyrazin-2-yl)oxy]phenyl}-2,3-dihydro-1,2-benzisothiazol-1,1-dioxide, 2-[3-fluoro-5-(pyrimidin-2-yloxy)phenyl]-2,3-dihydro-1,2-benzisothiazol-1,1-dioxide, 2-[3-fluoro-5-(1,3-thiazoyl-2-yloxy)phenyl]-2,3-dihydro-1,2-benzisothiazol-1,1-dioxide, 2-[3-fluoro-5-(pyrimidin-4-yloxy)phenyl]-2,3-dihydro-1,2-benzisothiazol-1,1-dioxide, 2-[3-(1,1-dioxide-1,2-benzisothiazol-2(3H)-yl)-5-fluorophenoxy]cyclohexanone, 2-[3-(1,1-dioxide-1,2-benzisothiazol-2(3H)-yl)-5-fluorophenoxy]cyclopentanone and 3-[3-(1,1-dioxide-1,2-benzisothiazol-2(3H)-yl)-5-fluorophenoxy]pyrrolidin-2-one.

A process for producing the compound according to the embodiment of the present invention will now be described.

A compound represented by a compound (I-1) according to the embodiment of the present invention:

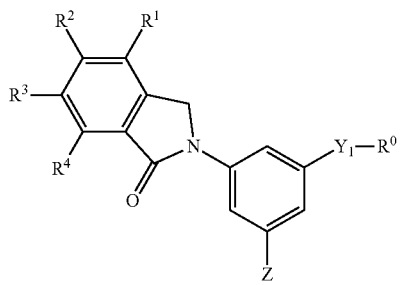

(I-1)

(wherein $R^0$ represents 5- or 6-membered heteroaryl having 1-3 hetero atoms selected from the group consisting of nitrogen, sulfur and oxygen atoms, contained within a ring, which 5- or 6-membered heteroaryl is optionally substituted with 1 to 3 same or different lower alkyl, lower alkoxy or halogen atoms, which lower alkyl and lower alkoxy may be substituted with 1 to 3 same or different halogen atoms; $Y_1$ represents an oxygen or sulfur atom; and the other symbols have the same definitions specified above) can be produced, for example, by the following process:

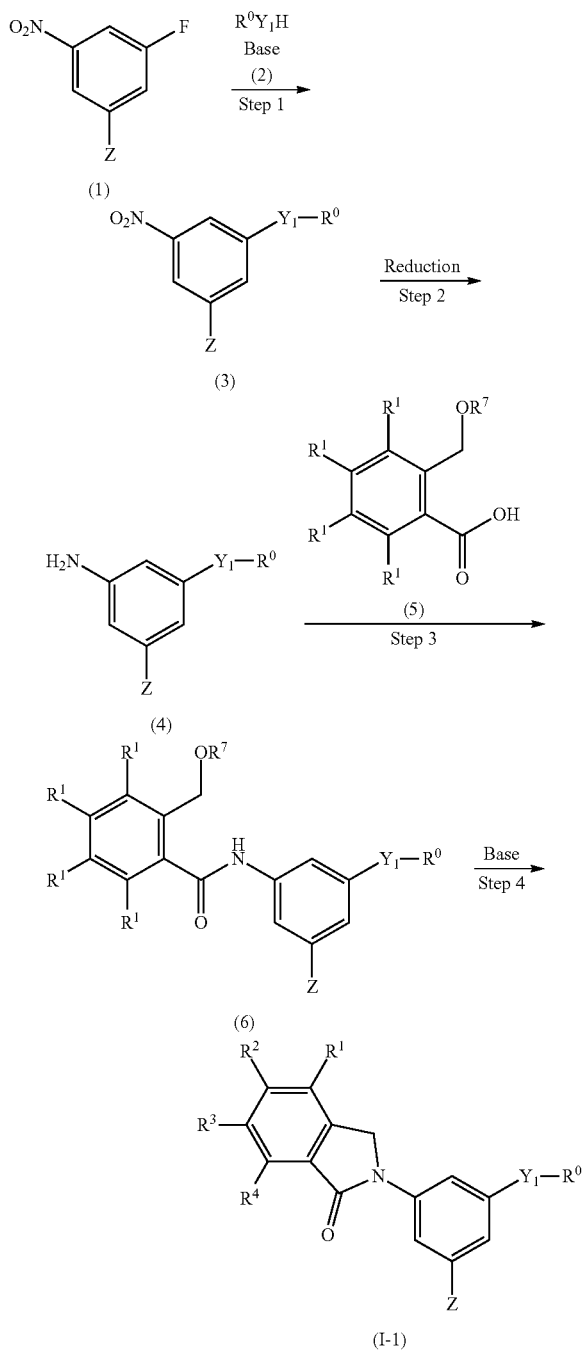

wherein $R^7$ represents lower alkyl or phenyl; and the other symbols have the same definitions specified above.

(Step 1)

This step is a process of producing a compound (3) by reacting a compound (1) with a compound (2) in the presence of base.

Examples of bases as used include potassium carbonate, sodium carbonate, cesium carbonate, sodium hydroxide, sodium hydride, potassium tert-butoxide, triethylamine, diisopropylethylamine and pyridine.

An amount of the base is typically 1-20 equivalents, preferably 1-5 equivalents, relative to 1 equivalent of the compound (1).

An amount of the compound (2) as used is typically 1-20 equivalents, preferably 1-5 equivalents, relative to 1 equivalent of the compound (1).

The reaction temperature is typically 0-150° C., preferably from room temperature to 80° C.

The reaction time is typically 0.1-72 hours, preferably 0.5-24 hours.

Unless interfering with the reaction, any reaction solvent may be used, examples of which include dimethylformamide (sometimes abbreviated as DMF), tetrahydrofuran (sometimes abbreviated as THF), toluene and N-methylpyrrolidone (sometimes abbreviated as NMP).

The compound (3) thus obtained may be isolated and purified in well-known separation and purification method such as concentration, concentration under reduced pressure, reprecipitation, solvent extraction, crystallization and chromatography, or subjected to the next step without isolation and purification.

(Step 2)

This step is a process for producing a compound (4) by reducing the compound (3).

For reductive reaction in this step, hydrogenation may be carried out in the presence of a metal catalyst.

As used herein, metal catalysts include, for example Raney nickel, platinum, palladium carbon and platinum dioxide.

An amount of the metal catalyst is typically 0.01-10 equivalents, preferably 0.1-2 equivalents, relative to 1 equivalent of the compound (1).

The reaction temperature is typically 0-100° C., preferably from room temperature to 60° C.

The reaction time is typically 0.1-72 hours, preferably 0.5-12 hours.

Unless interfering with the reaction, any reaction solvent may be used, examples of which include methanol, ethanol and THF.

The compound (4) thus obtained may be isolated and purified in well-known separation and purification method such as concentration, concentration under reduced pressure, reprecipitation, solvent extraction, crystallization and chromatography, or subjected to the next step without isolation and purification.

(Step 3)

This step is a process for producing a compound (6) by reacting the compound (4) with a compound (5) or a reactive derivative thereof.

For this reaction, typical amide formation reaction may be performed by methods as described in documents (e.g., Nobuo Izumiya, et al.: Peptide Gosei no Kiso to Jikken (Fundamentals and Experiments of Peptide Synthesis), Maruzen (1983); Comprehensive Organic Synthesis, Vol. 6, Pergamon Press (1991), etc.), methods equivalent thereto or combinations of these with usual methods, that is, by using a condensation agent that is well known to those skilled in the art, or by an ester activation method, a mixed anhydride method, an acid chloride method, a carbodiimide method, etc., which can be used by those skilled in the art. Examples of such amide formation reagents include thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate and benzotriazol-1-yl-oxy-tris(dimethylamino)phosphonium hexafluorophosphate;

especially preferably, for example thionyl chloride, 1-ethyl-3-(3-dimethylaminopropyl)carbodiimide hydrochloride, N,N-dicyclohexylcarbodiimide and benzotriazol-1-yl-oxy-tris(dimethylamino)phosphonium hexafluorophosphate. For the amide formation reaction, base and a condensation aid may be also used together with the amide formation reagent.

Bases as used include ternary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undeca-7-en (DBU) and 1,5-azabicyclo[4.3.0]nona-5-en (DBN); and aromatic amines such as pyridine, 4-dimethylaminopyridine, picoline, lutidine, quinoline and isoquinoline; especially preferably, e.g., ternary aliphatic amines, etc., particularly preferably, e.g., trimethylamine, N,N-diisopropylethylamine, etc.

Condensation aid as used include, for example, N-hydroxybenzotriazole hydrate, N-hydroxy succinimide, N-hydroxy-5-norbornen-2,3-dicarboximide and 3-hydroxy-3,4-dihydro-4-oxo-1,2,3-benzotriazole; especially preferably, e.g., N-hydroxybenzotriazole, etc.

An amount of the compound (4) as used is typically 1-10 equivalents, preferably 1-3 equivalents relative to 1 equivalent of the compound (5) or a reactive derivative thereof.

An amount of base as used is typically 1-10 equivalents, preferably 1-5 equivalents, depending on the types of a compound and a solvent used and other reaction conditions.

Unless interfering with the reaction, reaction solvents as used in this step, which are not particularly limited, include, e.g., inactive solvents; specifically, e.g., methylene chloride, chloroform, 1,2-dichloroethane, dimethylformamide, ethyl acetate, methyl acetate, acetonitrile, benzene, xylene, toluene, 1,4-dioxane, tetrahydrofuran and dimethoxyethane or mixed solvents thereof; preferably, e.g., methylene chloride, chloroform, 1,2-dichloroethane, acetonitrile and dimethylformamide, from the viewpoint of ensuring preferable reaction temperature.

The reaction time is typically 0.1-72 hours, preferably 0.5-24 hours.

The reaction temperature is typically from 0° C. to the boiling point of a solvent, preferably from room temperature to 80° C.

One or a combination of two or more of bases, amide formation reagents and condensation adjuvants as used in this step may be used.

The compound (6) thus obtained may be isolated and purified in well-known separation and purification method such as concentration, concentration under reduced pressure, reprecipitation, solvent extraction, crystallization and chromatography, or subjected to the next step without isolation and purification.

(Step 4)

This step is a process of producing a compound (I-1) by intramolecular cyclization of the compound (6) in the presence of base. Any $R^7$ in the compound (6) may be used if providing the compound (I-1) by intramolecular cyclization of the compound (6) by desorption as $OR^7$ in reaction in the step 4. Specifically, examples of $R^7$ in the compound (6) include lower alkyl, such as methyl or ethyl, and phenoxy.

Bases as used include the identical bases as used in Step 1.

An amount of the base used is typically 1-20 equivalents, preferably 1-5 equivalents, relative to 1 equivalent of the compound (6).

The reaction time is typically 0.1-72 hours, preferably 0.5-5 hours.

The reaction temperature is typically 0-200° C., preferably from room temperature to 150° C.

Unless interfering with the reaction, any reaction solvent may be used, examples of which specifically include DMF, THF, toluene and NMP.

The compound (I-1) thus obtained may be isolated and purified in well-known separation and purification method such as concentration, concentration under reduced pressure, reprecipitation, solvent extraction, crystallization and chromatography.

A compound (I-2) according to the embodiment of the present invention:

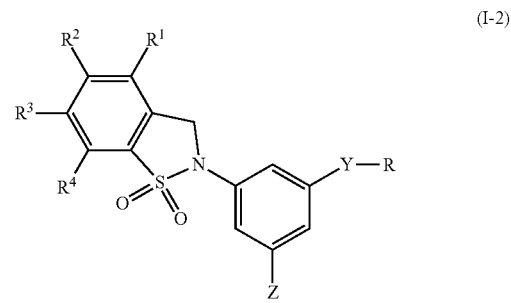

(I-2)

(wherein each symbol has the same definition specified above) can be also produced, e.g., by the following process:

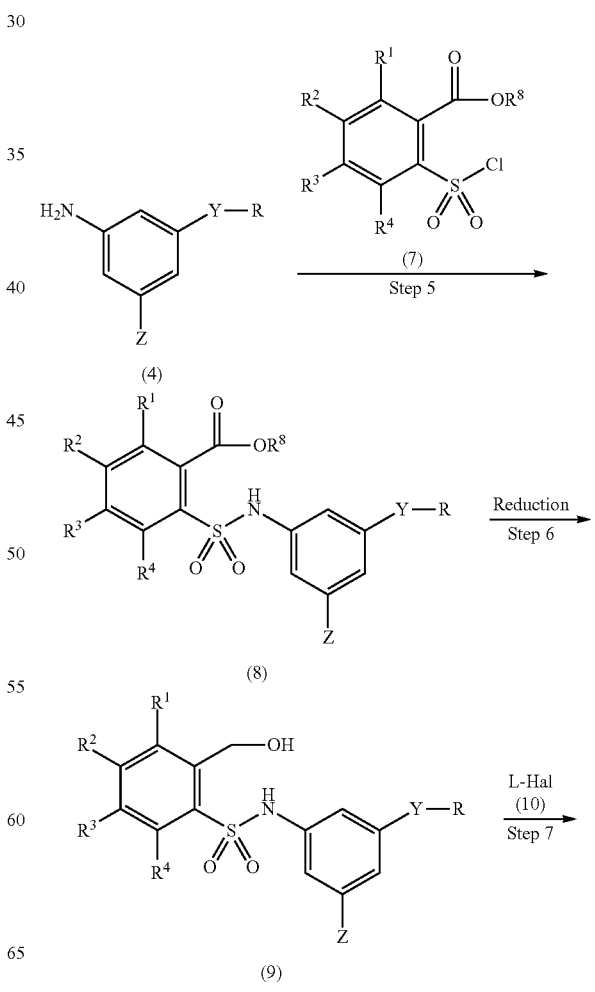

-continued

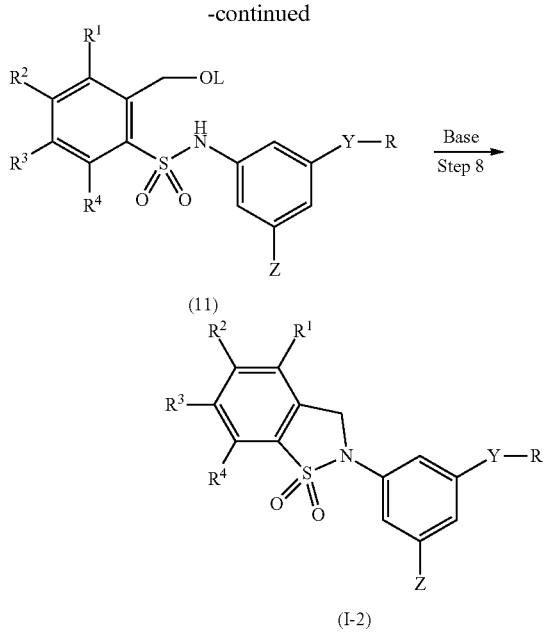

(wherein R⁸ represents lower alkyl; L represents $T_s$ or $M_s$; Hal represents a halogen atom; and the other symbols have the same definitions specified above).

(Step 5)

This step is a process for producing a compound (8) by reacting the compound (3) with the compound (5) in the presence of base.

Bases as used include the identical bases as used in Step 1.

An amount of the base as used is typically 0.1-50 equivalents, preferably 1-5 equivalents, relative to 1 equivalent of the compound (3).

An amount of the compound (5) as used is typically 1-50 equivalents, preferably 1-5 equivalents, relative to 1 equivalent of the compound (3).

The reaction temperature is typically 0-150° C., preferably from room temperature to 60° C.

The reaction time is typically 0.1-24 hours, preferably 0.1-2 hours.

Unless interfering with the reaction, any reaction solvent may be used, examples of which include methylene chloride, chloroform, dimethylformamide, toluene, 1,4-dioxane, tetrahydrofuran and pyridine.

The compound (8) thus obtained may be isolated and purified in well-known separation and purification method such as concentration, concentration under reduced pressure, reprecipitation, solvent extraction, crystallization and chromatography, or subjected to the next step without isolation and purification.

(Step 6)

This step is a process for producing a compound (9) by reducing the compound (8). Reducing agents as used include, e.g., diisobutylaluminum hydride and lithium aluminum hydride.

An amount of the reducing agent as used is typically 1-50 equivalents, preferably 1-5 equivalents, relative to 1 equivalent of the compound (8).

The reaction temperature is typically −78 to 80° C., preferably 0-50° C.

The reaction time is typically 0.1-24 hours, preferably 0.5-2 hours.

Unless interfering with the reaction, any reaction solvent may be used, examples of which include methylene chloride, chloroform, toluene and tetrahydrofuran.

The compound (9) thus obtained may be isolated and purified in well-known separation and purification method such as concentration, concentration under reduced pressure, reprecipitation, solvent extraction, crystallization and chromatography, or subjected to the next step without isolation and purification.

(Step 7)

This step is a process for producing a compound (11) according to an embodiment of the present invention by reacting the compound (9) with a compound (10) in the presence of base.

Bases as used include the identical bases as used in Step 1.

An amount of the base is typically 1-50 equivalents, preferably 1-5 equivalents, relative to 1 equivalent of the compound (9).

An amount of the compound (10) as used is typically 1-50 equivalents, preferably 1-5 equivalents, relative to 1 equivalent of the compound (9).

The reaction temperature is typically −50 to 100° C., preferably 0-50° C.

The reaction time is typically 0.1-24 hours, preferably 0.5-5 hours.

Unless interfering with the reaction, any reaction solvent may be used, examples of which include methylene chloride, chloroform, toluene, tetrahydrofuran and ethyl acetate.

The compound (11) thus obtained may be isolated and purified in well-known separation and purification method such as concentration, concentration under reduced pressure, reprecipitation, solvent extraction, crystallization and chromatography, or subjected to the next step without isolation and purification.

(Step 8)

This step is a process for producing the compound (I-2) according to the embodiment of the present invention by reacting the compound (11) with base.

Bases as used include the identical bases as used in Step 1.

An amount of the base is typically 1-100 equivalents, preferably 1-5 equivalents, relative to 1 equivalent of the compound (11).

The reaction temperature is typically 0-150° C., preferably from room temperature to 100° C.

The reaction time is typically 0.1-24 hours, preferably 0.5-4 hours.

Unless interfering with the reaction, any reaction solvent may be used, examples of which specifically include DMF, THF, toluene and NMP.

The compound (I-2) thus obtained may be isolated and purified by well-known separation and purification method such as concentration, concentration under reduced pressure, reprecipitation, solvent extraction, crystallization and chromatography, or subjected to the next step without isolation and purification.

A compound (I-3) according to the embodiment of the present invention:

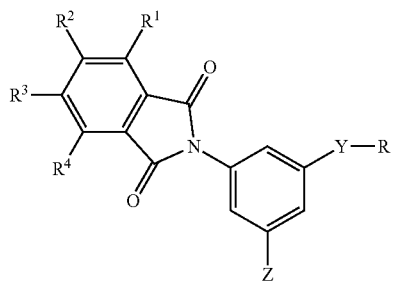

(wherein each symbol has the same definition specified above) can be also produced, e.g., by the following process:

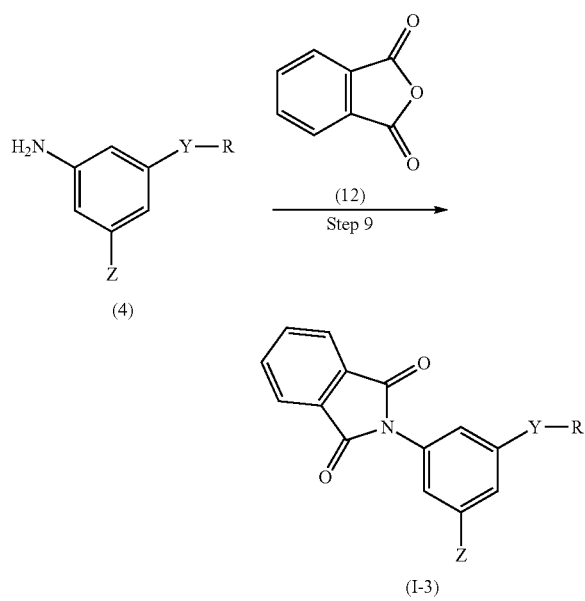

(wherein the other symbols have the same definitions specified above).

(Step 9)

This step is a process for producing a compound (I-3) according to an embodiment of the present invention by reacting the compound (4) with phthalic anhydride in the presence of acid.

As used herein, acids specifically include, e.g., acetic acid, hydrochloric acid, sulfuric acid, p-toluenesulfonic acid.

An amount of the acid is typically 0.1-100 equivalents, preferably 1-10 equivalents, relative to 1 equivalent of the compound (4).

An amount of phthalic anhydride as used is typically 1-100 equivalents, preferably 1-5 equivalents, relative to 1 equivalent of the compound (4).

The reaction time is typically 0.1-72 hours, preferably 1-12 hours.

The reaction temperature is typically 0-200° C., preferably from room temperature to the boiling point of a solvent.

Unless interfering with the reaction, any reaction solvent may be used, examples of which include DMF, THF, toluene and chloroform.

The compound (I-3) thus obtained may be isolated and purified in well-known separation and purification method such as concentration, concentration under reduced pressure, reprecipitation, solvent extraction, crystallization and chromatography.

A compound (I-2-1) according to the embodiment of the present invention can be also produced, e.g., by the following process:

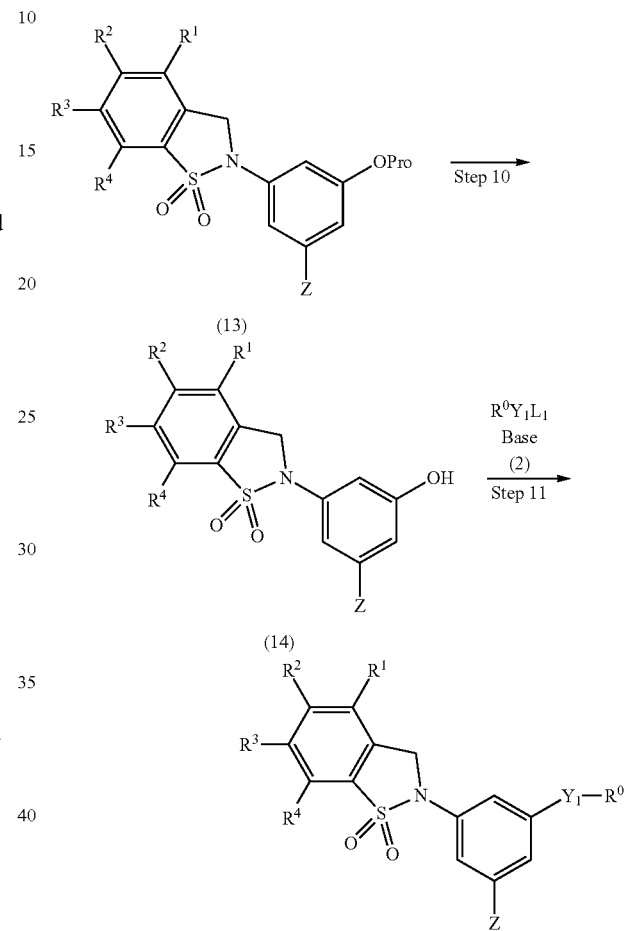

(wherein Pro represents a protective group for a hydroxy group; $L_1$ represents a leaving group; and the other symbols have the same definitions specified above).

(Step 10)

This step is a process for producing a compound (14) by removing a protective group Pro for a hydroxy group.

The reaction in this step can be carried out by a method as described in the document (T. W. Green: Protective Groups in Organic Synthesis, Second Edition, John Wiley & Sons (1991)), methods equivalent thereto or combinations of these with usual methods.

When a benzyl group is used as a protective group for a hydroxy group, the benzyl group can be removed by palladium carbon in methanol under hydrogen atmosphere.

The compound (14) thus obtained may be isolated and purified in well-known separation and purification method such as concentration, concentration under reduced pressure, reprecipitation, solvent extraction, crystallization and chromatography, or subjected to the next step without isolation and purification.

(Step 11)

This step is a process for producing the compound (I-2) according to the embodiment of the present invention by reacting the compound (14) with the compound (2) in the presence of base.

As used herein, bases include, for example potassium carbonate, sodium carbonate, cesium carbonate, sodium hydride, potassium-tert-butoxide, triethylamine and diisopropylethylamine.

An amount of the base is typically 1-100 equivalents, preferably 1-5 equivalents, relative to 1 equivalent of the compound (14).

An amount of the compound (2) as used is typically 1-100 equivalents, preferably 1-5 equivalents, relative to 1 equivalent of the compound (14).

The reaction temperature is typically 0-200° C., preferably from room temperature to 150° C.

The reaction time is typically 0.1-72 hours, preferably 1-24 hours.

Unless interfering with the reaction, any reaction solvent may be used, examples of which specifically include DMF, THF, toluene and NMP.

The compound (I-2) thus obtained may be isolated and purified in well-known separation and purification method such as concentration, concentration under reduced pressure, reprecipitation, solvent extraction, crystallization and chromatography, or subjected to the next step without isolation and purification.

The protective group can be introduced and removed by a method as described in the document (T. W. Green: Protective Groups in Organic Synthesis, Second Edition, John Wiley & Sons (1991)), methods equivalent thereto or combinations of these with usual methods.

Compounds in accordance with the embodiments of the present invention may be present as pharmaceutically acceptable salts, which can be produced according to usual methods using the compound represented by the formula (I), or (I-1), (I-2) or (I-3) encompassed thereby.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates.

When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc Furthermore, the compounds of the invention may also be in any other form of hydrates or solvates of their free compounds or their salts.

In contrast, a salt or ester can be also converted into a free compound by an ordinary method.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

In producing medicines for prevention and remedy for type II diabetes or diseases or symptoms associated with it, the compounds of formula (I) of the invention may be combined with carrier.

The dose of the compounds of formula (I) of the invention for prevention or remedy for diseases naturally varies, depending on the property of the symptom to which the treatment is directed, the specific compound selected for it and the administration route.

The dose also varies depending on the age, the body weight and the sensitivity of patients.

In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (I) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

Suspension for Injection (I.M.)

|  | mg/ml |
| --- | --- |
| compound of formula (I) | 10 |
| methyl cellulose | 5.0 |
| Tween 80 | 0.5 |
| benzyl alcohol | 9.0 |
| benzalkonium chloride | 1.0 |
| water for injection added to make 1.0 ml | |

TABLE 2

| Tablets | mg/tablet |
| --- | --- |
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

| Capsules | mg/capsule |
| --- | --- |
| compound of formula (I) | 25 |
| lactose powder | 573.5 |
| magnesium stearate | 1.5 |
| total | 600 mg |

TABLE 4

| Aerosol | per one container |
| --- | --- |
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other drugs usable not only for type II diabetes-associated diseases or symptoms but also for remedy/prevention/retardation of the onset of type II diabetes. The additional drugs may be administered in any administration route and dose generally employed in the art, simultaneously with or separately from the compound of formula (I).

In case where the compound of formula (I) is used along with one or more other drugs, then a pharmaceutical composition comprising the compound of formula (I) and the additional drug is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) other GPR120 agonist,
(b) glucokinase activators,
(c) bis-guanides (e.g., buformin, metoformin, fenformin,),
(d) PPAR agonists (e.g., triglytazon, pioglytazon, rosiglytazon),
(e) insulin,
(f) somatostatin,
(g) α-glucosidase inhibitors (e.g., boglybose, miglytol, acarbose),
(h) insulin secretion promoters (e.g., acetohexamide, calbutamide, chlorpropamide, glybomlide, glycrazide, glymerpiride, glypidide, glyquidine, glysoxepide, glyburide, glyhexamide, glypinamide, fenbutamide, trazamide, tolbutamide, tolcyclamide, nateglynide, repaglynide),
(i) DPP-IV (dipeptidyl peptidase IV) inhibitors, and The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual ingredients should be in the combination.

The compound according to an embodiment of the present invention has a GPR120 function regulating action, wherein "GPR120 function regulating action" means activation or suppression of the function of a GPR120 receptor. For example, a GPR120 agonist is also included in compounds having the GPR120 function regulating action.

A compound according to an embodiment of the present invention or a pharmaceutically acceptable salt thereof has a GPR120 function regulating action, particularly a GPR120 agonist action, and is useful for treating and/or preventing diabetes mellitus or hyperlipidemia.

It should be understood by those skilled in the art that various modifications, combinations, sub-combinations and alterations may occur depending on design requirements and other factors insofar as they are within the scope of the appended claims or the equivalents thereof.

EXAMPLES

The present invention is described below in more detail referring to Formulation Examples, Examples and Reference Examples, but is not limited thereto.

Formulation Example 1

Ten parts of the compound in accordance with Example 1, 15 parts of heavy magnesium oxide and 75 parts of lactose are blended uniformly to prepare a powder having a particle size of 350 μm or less in powder or granular form. The powder is charged in a capsule container to form a capsule.

Formulation Example 2

After uniformly blending 45 parts of the compound in accordance with Example 1, 15 parts of starch, 16 parts of lactose, 21 parts of crystalline cellulose, 3 parts of polyvinylalcohol and 30 parts of distilled water, the blend is crushed into granules, which are dried and then sieved to form granules having a particle diameter of 177-1410 μm.

Formulation Example 3

After preparing granules in the same manner as in Formulation Example 2, 3 parts of calcium stearate is added to 96 parts of the granules, and the mixture is compression-molded to prepare tablets having a diameter of 10 mm.

Formulation Example 4

To 90 parts of the granules prepared by the method described in Formulation Example 2 is added 10 parts of crystalline cellulose and 3 parts of calcium stearate, and the mixture is compression-molded to form tablets having a diameter of 8 mm, to which a syrup gelatin/precipitated calcium carbonate suspension is added to prepare sugar-coated tablets.

Wakogel (registered trademark) C-300, made by Wako Pure Chemical Industries Ltd., or KP-Sil (Registered Trademark) Silica prepacked column, made by Biotage, was used for the silica gel column chromatography in Examples. Kieselgel™ 60 $F_{254}$, Art. 5744, made by Merck & Co., was used for preparative thin layer chromatography. Chromatorex (registered trademark) NH (100-250 mesh or 200-350 mesh), made by Fuji Silysia Chemical Ltd., was used for basic silica gel column chromatography.

$^1$H-NMR was measured using Gemini (200 MHz, 300 MHz), Mercury (400 MHz) and Inova (400 MHz), made by Varian, using tetramethylsilane as a standard substance. In addition, the mass spectra were measured by electrospray ionization (ESI) or atmospheric pressure chemical ionization (APCI) using Micromass ZQ made by Waters.

The meanings of the abbreviations in Examples are shown below.

i-Bu=isobutyl
n-Bu=n-butyl
t-Bu=tert-butyl
Boc=tert-butoxycarbonyl
Me=methyl
Et=ethyl
Ph=phenyl
i-Pr=isopropyl
n-Pr=n-propyl
$CDCl_3$=heavy chloroform
$CD_3OD$=heavy methanol
DMSO-$d_6$=heavy dimethylsulfoxide The meanings of the abbreviations in the nuclear magnetic resonance spectra are shown below.

s=singlet
d=doublet
dd=double doublet
dt=double triplet
ddd=double double doublet
Sept=septet
t=triplet
m=multiplet
br=broad
brs=broad singlet
q=quartet
J=coupling constant
Hz=hertz Example 1

Synthesis of 2-[3-fluoro-5-(pyridin-3-yloxy)phenyl]isoindolin-1-one

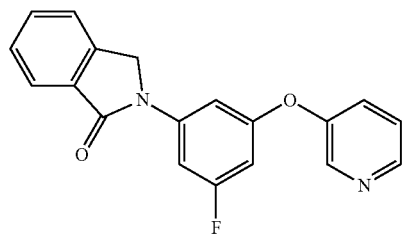 [SMILES: O=C1c2ccccc2CN1c1cc(F)cc(Oc2cccnc2)c1]

(1) Synthesis of 3-(3-fluoro-5-nitrophenoxy)pyridine

To a solution of 3-hydroxypyridine (3.25 g) in dimethylformamide (75 ml), 6.75 g of potassium carbonate and 5.0 g of 1,3-difluoro-5-nitrobenzene were added, and the reaction solution was stirred at 100° C. for 6 hours. The reaction solution was cooled, thereafter diluted with a saturated aqueous ammonium chloride solution, and extracted with ethyl acetate. The combined organic layers were washed with water and a saturated saline solution and dried over anhydrous sodium sulfate. The solvent was distilled off under reduced pressure, and the resultant residue was purified by silica gel chromatography to yield the title compound as a yellow oil.

¹H-NMR(CDCl₃)δ:7.05(1H,dt,J=8.6,2.4 Hz),7.39-7.45 (2H,m),7.62-7.64(1H,m),7.70(1H,dt,J=8.2,2.2 Hz), 8.49 (1H,d,J=2.2 Hz),8.55(1H,dd,J=4.4,2.2 Hz).
ESI-MS Found:m/z 235.1[M+H]+

(2) Synthesis of 3-fluoro-5-(pyridine-3-yloxy)aniline

A palladium-carbon catalyst was added to a solution of 3-(3-fluoro-5-nitrophenoxy)pyridine (8.0 g) in methanol (70 ml), and the reaction solution was stirred under hydrogen atmosphere at room temperature for 2 hours. The reaction solution was filtered through Celite, and the filtrate was distilled off under reduced pressure to obtain a crude product as a yellow oil.

(3) Synthesis of 2-[3-fluoro-5-(pyridin-3-yloxy)phenyl]isoindolin-1-one

To a solution of 3-fluoro-5-(pyridine-3-yloxy)aniline (200 mg) in pyridine (5.0 ml), 230 mg of 2-(phenoxymethyl)benzoic acid and 250 mg of 1-ethyl-3-(3-dimethylaminopropyl) carbodiimide were added, and the reaction solution was stirred at room temperature for 1 hour. Water and a saturated aqueous ammonium chloride solution were added to the reaction solution, and the mixture was extracted with ethyl acetate. The combined organic layers were washed with a 1N aqueous hydrochloric acid solution and a saturated saline solution and dried over anhydrous magnesium sulfate. The solvent was distilled off under reduced pressure to obtain a crude product as colorless oil. To a solution of the obtained crude product in N-methylpyrrolidone (5.0 ml) was added 410 mg of potassium carbonate, and the mixture was stirred at 120° C. for 8 hours. The reaction solution was cooled, thereafter diluted with a saturated aqueous ammonium chloride solution, and extracted with ethyl acetate. The combined organic layers were washed with water and a saturated saline solution and dried over anhydrous sodium sulfate. The solvent was distilled off under reduced pressure, and the resultant residue was purified by silica gel chromatography to yield the title compound as a white solid.
¹H-NMR(CDCl₃)δ:4.77(2H,s),6.46-6.50(1H,m),7.30(1H, dd,J=8.3,4.6 Hz),7.35-7.40(2H,m),7.46-7.53(3H,m),7.56-7.61(1H,m),7.87(1H,d,J=7.8 Hz),8.38-8.45(2H,m).
ESI-MS Found:m/z 321.0[M+H]+

Example 2

Synthesis of 2-[3-fluoro-5-(pyridin-3-yloxy)phenyl]-2,3-dihydro-1,2-benzisothiazol-1,1-dioxide

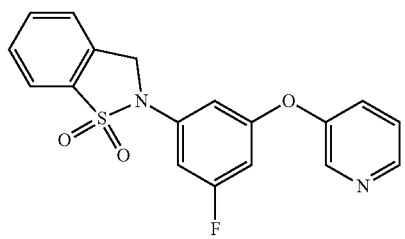 [SMILES: O=S1(=O)c2ccccc2CN1c1cc(F)cc(Oc2cccnc2)c1]

(1) Synthesis of methyl 2-({[3-fluoro-5-(pyridin-3-yloxy)phenyl]amino}sulfonyl)benzoate To a solution of 3-fluoro-5-(pyridin-3-yloxy)aniline (1.10 g) in pyridine (22 ml), 1.92 g of methyl 2-(chlorosulfonyl) benzoate was added, and the reaction solution was stirred overnight at room temperature. Water and a saturated aqueous ammonium chloride solution were added to the reaction solution, and the mixture was extracted with ethyl acetate. The combined organic layers were washed with a 1N aqueous hydrochloric acid solution and a saturated saline solution and dried over anhydrous magnesium sulfate. The solvent was distilled off under reduced pressure, and the resultant residue was purified by silica gel chromatography to yield the title compound as a white solid.
¹H-NMR(CDCl₃)δ:4.03(3H,s),6.43(1H,dt,J=9.4,2.2 Hz), 6.65-6.67(1H,m),6.75(1H,dt,J=9.4,2.2 Hz),7.23-7.31(2H, m),7.57-7.67(2H,m),7.85(1H,dd,J=7.3,1.5 Hz),7.91(1H,dd, J=7.8,1.5 Hz),8.20(1H,brs),8.28-8.30(1H,m),8.42(1H,dd, J=4.6,1.7 Hz).
ESI-MS Found:m/z 403.2[M+H]+

(2) Synthesis of N-[3-fluoro-5-(pyridin-3-yloxy) phenyl]-2-(hydroxymethyl)benzenesulfonamide A solution of 1.0M diisobutylaluminum hydride in tetrahydrofuran (7.50 ml) was added to a solution of methyl 2-({[3-fluoro-5-(pyridin-3-yloxy)phenyl]amino}sulfonyl)benzoate (1.50 g) in tetrahydrofuran (22 ml) at 0° C., and the reaction solution was stirred at the same temperature for 1 hour. A saturated aqueous solution of Rochelle salt and ethyl acetate were added to the reaction solution, and the mixture was stirred for 30 minutes, followed by being extracted with ethyl acetate. The combined organic layers were washed with a saturated saline solution and dried over anhydrous magnesium sulfate. The solvent was distilled off under reduced pressure, and the resultant residue was purified by silica gel chromatography to yield the title compound as a colorless oily substance.
¹H-NMR(DMSO-D₆)δ:4.84(2H,s),6.18-6.24(1H,m),6.29 (1H,brs),6.42(1H,d,J=11.7 Hz),7.30(1H,t,J=7.6 Hz),7.34-7.38(1H,m),7.40-7.43(1H,m),7.49(1H,t,J=7.6 Hz),7.61(1H, d,J=7.3 Hz),7.69(1H,dd,J=7.6,1.2 Hz),8.30(1H,d,J=2.4 Hz), 8.39(1H,dd,J=4.4,1.5 Hz).
ESI-MS Found:m/z 375.1[M+H]+

(3) Synthesis of 2-[3-fluoro-5-(pyridin-3-yloxy)phenyl]-2,3-(dihydro)-1,2-benzisothiazol-1,1-dioxide To a solution of N-[3-fluoro-5-(pyridine-3-yloxy)phenyl]-2-(hydroxymethyl)benzenesulfonamide (1.39 g) in ethyl acetate (20 ml), 1.30 ml of triethylamine and 0.36 ml of methanesulfonyl chloride were added, and the reaction solution was stirred at room temperature for 1 hour. The reaction solution was filtered through Celite, and the filtrate was distilled off under reduced pressure to obtain a crude product as a colorless oil. To a solution of the obtained crude product in dimethylformamide (20 ml), 920 mg of potassium carbonate was added, and the mixture was stirred at room temperature for 1 hour. A saturated aqueous ammonium chloride solution was added to the reaction solution, and the mixture was extracted with ethyl acetate. The combined organic layers were washed with water and a saturated saline solution and dried over anhydrous magnesium sulfate. The resultant residue was purified by silica gel chromatography to yield the title compound as a white solid.
¹H-NMR(CDCl₃)δ:4.83(2H,s),6.47(1H,dt,J=9.6,2.1 Hz), 6.91-6.93(1H,m),7.01(1H,dt,J=10.1,2.1 Hz),7.32-7.35(1H, m),7.38-7.42(1H,m),7.51(1H,d,J=7.8 Hz),7.62(1H,t,J=7.6 Hz),7.69-7.73(1H,m),7.88(1H,d, J=7.8 Hz),8.46(1H,dd, J=4.6,1.2 Hz),8.48(1H,d,J=2.9 Hz).
ESI-MS Found:m/z 357.3[M+H]+

Example 3

Synthesis of 2-[3-fluoro-5-(pyridin-3-yloxy)phenyl]-1H-isoindol-1,3(2H)-dione

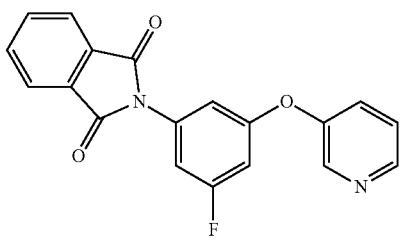 [SMILES: O=C1c2ccccc2C(=O)N1c1cc(F)cc(Oc2cccnc2)c1]

To a solution of 3-fluoro-5-(pyridine-3-yloxy)aniline (330 mg) in acetic acid (5.0 ml), 160 mg of phthalic anhydride was added, the reaction solution was stirred overnight at 100° C. The reaction solution was cooled, followed by adding a saturated aqueous sodium bicarbonate solution and extracting the mixture with chloroform. The combined organic layers were washed with water and a saturated saline solution and dried over anhydrous magnesium sulfate. The solvent was distilled off under reduced pressure, and the resultant residue was purified by silica gel chromatography to yield the title compound as a white solid.

$^1$H-NMR(CDCl$_3$)δ:6.70-6.74(1H,m),6.96(1H,s),7.00-7.05(1H,m),7.31(1H,dd,J=8.4,4.6 Hz),7.40(1H,d, J=8.4 Hz), 7.78(2H,dd,J=5.3,3.1 Hz),7.92(2H,dd,J=5.3,3.1 Hz),8.42 (1H,d,J=4.3 Hz),8.45-8.47(1H,m).

ESI-MS Found:m/z 335.1[M+H]+

Example 4

Synthesis of 2-[3-fluoro-5-(pyrazin-2-yloxy)phenyl]-2,3-dihydro-1,2-benzisothiazol-1,1-dioxide

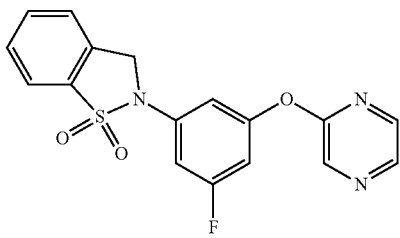 [SMILES: O=S1(=O)c2ccccc2CN1c1cc(F)cc(Oc2cnccn2)c1]

(1) Synthesis of 2-[3-(benzyloxy)-5-fluorophenyl]-2,3-dihydro-1,2-benzisothiazol-1,1-dioxide The title compound was obtained as a white solid by the methods as in Example 1 (1) and (2) and Examples (1)-(3), methods equivalent thereto or combinations of these with usual methods, using benzyl alcohol.

(2) Synthesis of 3-(1,1-dioxide-1,2-benzisothiazol-2(3H)-yl)-5-fluorophenol

A palladium-carbon catalyst was added to a solution of 2-[3-(benzyloxy)-5-fluorophenyl]-2,3-dihydro-1,2-benzisothiazol-1,1-dioxide (800 mg) in methanol (10.0 ml), and the reaction solution was stirred under hydrogen atmosphere at room temperature for 1.5 hours. The reaction solution was filtered through Celite, and the filtrate was distilled off under reduced pressure to obtain a crude product as a white solid.

$^1$H-NMR(DMSO-D$_6$)δ:5.03(2H,s),6.38(1H,dt,J=10.8,2.2 Hz),6.65(1H,dt,J=10.8,2.2 Hz),6.78-6.80(1H, m),7.66-7.70 (2H,m),7.79-7.83(1H,m),7.99(1H,d,J=8.3 Hz),10.21(1H, brs).

(3) Synthesis of 2-[3-fluoro-5-(pyrazin-2-yloxy)phenyl]-2,3-dihydro-1,2-benzisothiazol-1,1-dioxide Potassium carbonate and 2-chloropyrazine were added to a solution of 3-(1,1-dioxide-1,2-benzisothiazol-2(3H)-yl)-5-fluorophenol in dimethylformamide, and the reaction solution was stirred overnight at 80° C. The reaction solution was cooled, there after diluted with a saturated aqueous ammonium chloride solution, and extracted with ethyl acetate. The combined organic layers were washed with water and a saturated saline solution and dried over anhydrous magnesium sulfate. The solvent was distilled off under reduced pressure, and the resultant residue was purified by silica gel chromatography to yield the title compound as a yellow oily substance.

$^1$H-NMR(CDCl$_3$)δ:4.86(2H,s),6.74(1H,dt,J=9.3,2.0 Hz), 7.07-7.12(2H,m),7.51(1H,d,J=7.3 Hz),7.60-7.64(1H,m), 7.68-7.73(1H,m),7.89(1H,d,J=7.8 Hz),8.15(1H,dd,J=2.9,1.5 Hz),8.33(1H,d,J=2.9 Hz),8.47-8. 49(1H,m).

ESI-MS Found:m/z 358.1[M+H]+

Example 5

Synthesis of 4-fluoro-2-[3-fluoro-5-(pyridin-3-yloxy)phenyl]-1H-1,3(2H)-dione

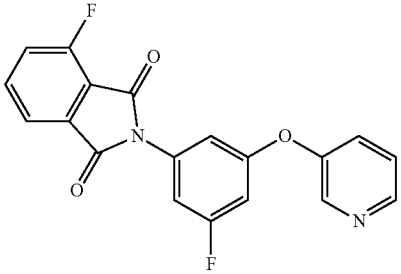 [SMILES: O=C1c2cccc(F)c2C(=O)N1c1cc(F)cc(Oc2cccnc2)c1]

The title compound was obtained as a white solid by the method as in Example 3, methods equivalent thereto or combinations of these with usual methods, using 3-fluorophthalic anhydride.

1H-NMR(CDCl3)δ:6.74(1H,d,J=9.6 Hz),6.93(1H,s),7.00 (1H,d,J=9.6 Hz),7.31(1H,dd,J=8.4,4.7 Hz),7.38-7.47(2H, m),7.72-7.81(2H,m),8.42(1H,d,J=4.7 Hz),8.46(1H,d,J=2.2 Hz).

ESI-MS Found:m/z 353.1[M+H]+

Example 6

Synthesis of 7-fluoro-2-[3-fluoro-5-(pyridin-3-yloxy)phenyl]isoindolin-1-one

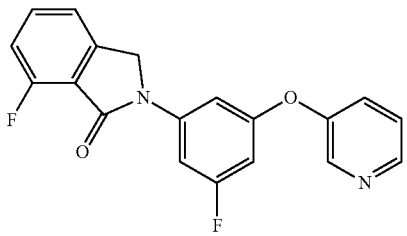 [SMILES: O=C1c2c(F)cccc2CN1c1cc(F)cc(Oc2cccnc2)c1]

The title compound was obtained as a white solid by the method as in Example 1 (3), methods equivalent thereto or combinations of these with usual methods, using 2-fluoro-6-phenoxymethylbenzoic acid.

$^1$H-NMR(CDCl$_3$)δ:4.78(2H,s),6.50(1H,dt,J=9.2,2.2 Hz), 7.11(1H,t,J=8.8 Hz),7.25-7.32(2H,m),7.35-7.39(2H,m),7.45 (1H,dt,J=10.8,2.2 Hz),7.53-7.59(1H,m),8.38-8.43(2H,m).

ESI-MS Found:m/z 339.4[M+H]+

Example 7

Synthesis of 4-fluoro-2-[3-fluoro-5-(pyridin-3-yloxy)phenyl]isoindolin-1-one

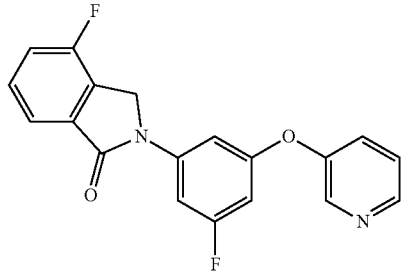 [SMILES: O=C1c2cccc(F)c2CN1c1cc(F)cc(Oc2cccnc2)c1]

The title compound was obtained as a white solid by the method as in Example 1 (3), methods equivalent thereto or combinations of these with usual methods, using 3-fluoro-2-phenoxymethylbenzoic acid.

$^1$H-NMR(CDCl$_3$)δ:4.82(2H,s),6.50(1H,dt,J=9.2,2.2 Hz), 7.26-7.33(2H,m),7.38(2H,d,J=8.8 Hz),7.48(2H, dt,J=10.6, 2.2 Hz),7.68(1H,d,J=7.6 Hz),8.40-8.44(2H,m).

ESI-MS Found:m/z 339.4[M+H]+

Example 8

Synthesis of 5-fluoro-2-[3-fluoro-5-(pyridin-3-yloxy)phenyl]isoindolin-1-one

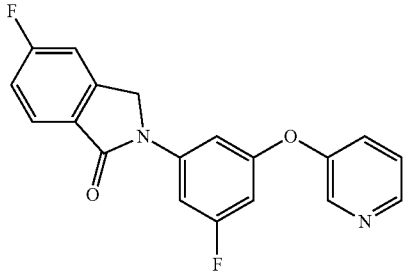 [SMILES: O=C1c2ccc(F)cc2CN1c1cc(F)cc(Oc2cccnc2)c1]

The title compound was obtained as a white solid by the method as in Example 1 (3), methods equivalent thereto or combinations of these with usual methods, using 4-fluoro-2-phenoxymethylbenzoic acid.

$^1$H-NMR(CDCl$_3$)δ:4.75(2H,s),6.48(1H,dt,J=9.4,2.2 Hz), 7.15-7.20(2H,m),7.30(1H,dd,J=8.9,4.2 Hz),7.34-7.39(2H, m),7.47(1H,dt,J=11.0,2.2 Hz),7.85(1H,dd,J=8.9,5.2 Hz), 8.40-8.45(2H,m).

ESI-MS Found:m/z 339.4[M+H]+

Example 9

Synthesis of 2-[3-fluoro-(pyridin-3-yloxy)phenyl]-1,2-benzisothiazol-3(2H)-one-1,1-dioxide

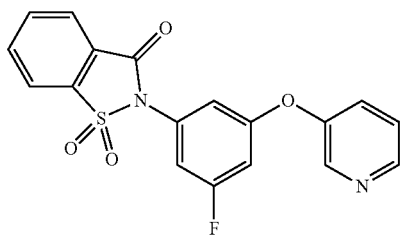 [SMILES: O=C1c2ccccc2S(=O)(=O)N1c1cc(F)cc(Oc2cccnc2)c1]

The title compound was obtained as a white solid by the method as in Example 2 (1), methods equivalent thereto or combinations of these with usual methods, using methyl 2-chlorosulfonylbenzoate.

$^1$H-NMR(CDCl$_3$)δ:6.81(1H,dt,J=9.5,2.1 Hz),7.02(1H,s), 7.08(1H,dt,J=8.6,2.1 Hz),7.33(1H,dd,J=8.2,4.7 Hz),7.42 (1H,d,J=8.2 Hz),7.85-7.98(3H,m),8.13(1H,d,J=7.2 Hz), 8.43-8.50(2H,m).

ESI-MS Found:m/z 371.1[M+H]+

Example 10

Synthesis of 2-{3-fluoro-5-[(6-methylpyridin-3-yl)oxy]phenyl}isoindolin-1-one

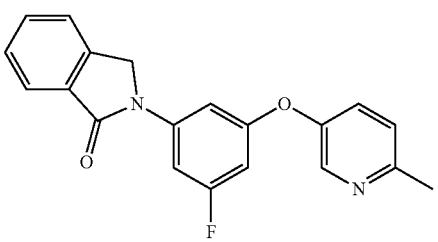 [SMILES: Cc1ccc(Oc2cc(F)cc(N3Cc4ccccc4C3=O)c2)cn1]

The title compound was obtained as a white solid by the methods as in Example 1 (1)-(3), methods equivalent thereto or combinations of these with usual methods, using 3-hydroxy-6-methylpyridine.

$^1$H-NMR(CDCl$_3$)δ:2.54(3H,s),4.75(2H,s),6.43(1H,dt, J=9.5,2.2 Hz),7.15(1H,d,J=8.5 Hz),7.28(1H,dd,J=8.5,2.8 Hz),7.32-7.35(1H,m),7.45-7.49(3H,m),7.55-7.60(1H,m), 7.86(1H,d,J=7.6 Hz),8.31(1H,d,J=2.8 Hz).

ESI-MS Found:m/z 335.2[M+H]+

Example 11

Synthesis of 2-{3-fluoro-5-[(3-methylpyrazin-2-yl)oxy]phenyl}-2,3-dihydro-1,2-benzisothiazol-1,1-dioxide

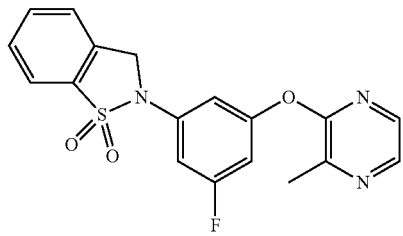 [SMILES: Cc1nccnc1Oc1cc(F)cc(N2Cc3ccccc3S2(=O)=O)c1]

The title compound was obtained as a white solid by the method as in Example 4, methods equivalent thereto or combinations of these with usual methods, using 2-chloro-3-methylpyrazine.

$^1$H-NMR(CDCl$_3$)δ:2.66(3H,s),4.87(2H,s),6.72(1H,dt, J=9.1,2.2 Hz),7.05-7.09(2H,m),7.51(1H,d,J=7.8 Hz),7.62 (1H,t,J=7.8 Hz),7.71(1H,t,J=7.8 Hz),7.89(1H,d,J=7.8 Hz), 7.94(1H,d,J=2.4 Hz),8.20(1H,d,J=2.4 Hz).

ESI-MS Found:m/z 372.4[M+H]+

Example 12

Synthesis of 2-[3-fluoro-5-(pyrimidin-2-yloxy)phenyl]-2,3-dihydro-1,2-benzisothiazol-1,1-dioxide

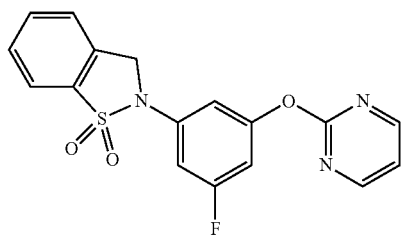 [SMILES: O=S1(=O)c2ccccc2CN1c1cc(F)cc(Oc2ncccn2)c1]

The title compound was obtained as a white solid by the method as in Example 4, methods equivalent thereto or combinations of these with usual methods, using 2-chloropyrimidine.

$^1$H-NMR(CDCl$_3$)δ:4.87(2H,s),6.79(1H,dt,J=9.1,2.2 Hz), 7.07-7.12(2H,m),7.16(1H,dt,J=10.2,2.2 Hz),7. 51(1H,d, J=7.8 Hz),7.62(1H,t,J=7.6 Hz),7.70(1H,td,J=7.6,1.1 Hz), 7.89(1H,d,J=7.8 Hz),8.60(2H,d,J=4.9 Hz).

ESI-MS Found:m/z 358.4[M+H]+

Example 13

Synthesis of 2-[3-fluoro-5-(1,3-thiazol-2-yloxy)phenyl]-2,3-dihydro-1,2-benzisothiazol-1,1-dioxide

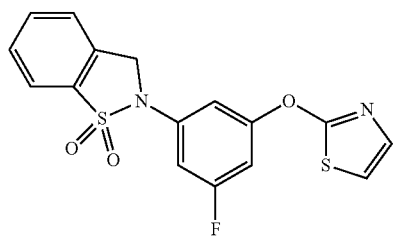 [SMILES: O=S1(=O)c2ccccc2CN1c1cc(F)cc(Oc2nccs2)c1]

The title compound was obtained as a white solid by the method as in Example 4, methods equivalent thereto or combinations of these with usual methods, using 2-bromothiazole.

$^1$H-NMR(DMSO-D$_6$)δ:5.08(2H,s),7.09-7.15(2H,m), 7.19-7.21(1H,m),7.27-7.31(2H,m),7.62-7.67(2H, m),7.78 (1H,t,J=7.6 Hz),7.98(1H,d,J=7.8 Hz).

ESI-MS Found:m/z 363.0[M+H]+

Example 14

Synthesis of 2-[3-fluoro-5-(pyrimidin-4-yloxy)phenyl]-2,3-dihydro-1,2-benzisothiazol-1,1-dioxide

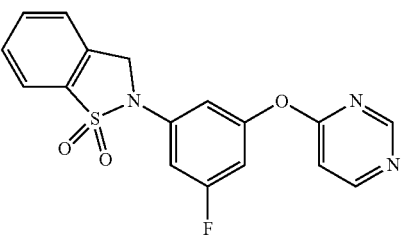 [SMILES: O=S1(=O)c2ccccc2CN1c1cc(F)cc(Oc2ccncn2)c1]

The title compound was obtained as a white solid by the method as in Example 4, methods equivalent thereto or combinations of these with usual methods, using 4-chloropyrimidine.

$^1$H-NMR(CDCl$_3$)δ:4.87(2H,s),6.75(1H,dt,J=8.9,2.1 Hz), 6.97-7.00(1H,m),7.07-7.09(1H,m),7.12(1H,dt, J=10.1,2.1 Hz),7.51(1H,d,J=7.8 Hz),7.63(1H,t,J=7.6 Hz),7.69-7.74(1H, m),7.89(1H,d,J=7.8 Hz),8.64(1H, d,J=5.9 Hz),8.82(1H,s).

ESI-MS Found:m/z 358.1[M+H]+

Example 15

Synthesis of 2-[3-(1,1-dioxide-1,2-benzisothiazol-2(3H)-yl)-5-fluorophenoxy]cyclohexanone

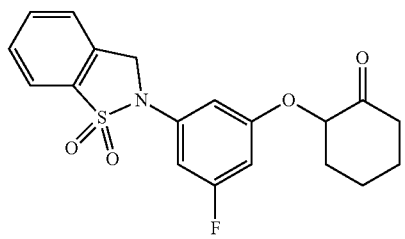 [SMILES: O=C1CCCCC1Oc1cc(F)cc(N2Cc3ccccc3S2(=O)=O)c1]

The title compound was obtained as a white solid by the method as in Example 4, methods equivalent thereto or combinations of these with usual methods, using 2-chlorocyclohexanone.

$^1$H-NMR(DMSO-D$_6$)δ:1.53-1.56(1H,m),1.74-1.85(3H,m),1.96-2.01(1H,m),2.27-2.35(2H,m),2.61(1H, td,J=13.5, 7.0 Hz),5.03(2H,s),5.05-5.10(1H,m),6.58(1H,dt,J=9.5,2.1 Hz),6.75-6.82(2H,m),7.63-7.68(2H, m),7.79(1H,t,J=7.3 Hz),7.96(1H,d,J=7.6 Hz).

ESI-MS Found:m/z 376.1[M+H]+

Example 16

Synthesis of 2-[3-(1,1-dioxide-1,2-benzisothiazol-2(3H)-yl)-5-fluorophenoxy]cyclopentanone

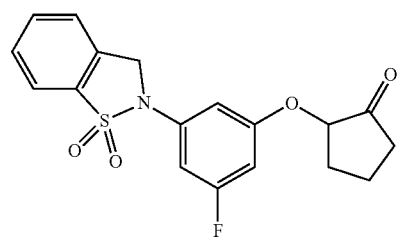 [SMILES: O=C1CCCC1Oc1cc(F)cc(N2Cc3ccccc3S2(=O)=O)c1]

The title compound was obtained as a white solid by the method as in Example 4, methods equivalent thereto or combinations of these with usual methods, using 2-chlorocyclopentanone.

$^1$H-NMR(DMSO-D$_6$)δ:1.77-1.84(2H,m),1.94-1.97(1H,m),2.19-2.31(3H,m),4.97(1H,t,J=8.9 Hz),5.04(2H,s),6.73 (1H,dt,J=10.2,2.1 Hz),6.82-6.86(2H,m),7.64-7.68(2H,m),7.79(1H,t,J=7.6 Hz),7.96(1H,d,J=8.2 Hz).

ESI-MS Found:m/z 362.2[M+H]+

Example 17

Synthesis of 3-[3-(1,1-dioxide-1,2-benzisothiazol-2(3H)-yl)-5-fluorophenoxy]pyrrolidin-2-one

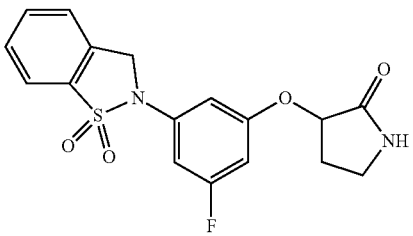 [SMILES: O=C1NCCC1Oc1cc(F)cc(N2Cc3ccccc3S2(=O)=O)c1]

The title compound was obtained as a white solid by the method as in Example 4, methods equivalent thereto or combinations of these with usual methods, using 3-chloropyrrolidin-2-one.

$^1$H-NMR(DMSO-D$_6$)δ:1.96-2.02(1H,m),2.49-2.51(1H,m),3.20-3.22(2H,m),4.96(1H,t,J=7.6 Hz),5.04(2H,s),6.78 (1H,dt,J=10.2,2.1 Hz),6.83-6.87(2H,m),7.65-7.67(2H,m),7.79(1H,t,J=7.8 Hz),7.96(1H,d,J=8.5 Hz),8.03-8.06(1H,brm).

ESI-MS Found:m/z 363.1[M+H]+

The usefulness of the compound encompassed by formula (I) for a medicament is shown in tests described below.

The usefulness of the compound according to an embodiment of the present invention was assessed for a medicament by described methods of the following in vitro tests:

Test 1: Cloning of Genes

Primers were synthesized in the domains on the opposite sides of the base sequences of the ORFs of the known GPCR and GPR120 in GenBank Accession NOs. NM 181745 (human) and NM 181748 (mouse), and the genes were cloned by RT-PCR. The base sequences of the primers used are described below. The restriction enzymes, BamHI and EcoRI, recognition sites were introduced for subcloning, respectively.

```
hGPR120_F01:
                                    (SEQ ID NO: 1)
AGGATCCGCCGCCATGTCCCCTGAATGCGCGCGGGCAG hGPR120_R01:
                                    (SEQ ID NO: 2)
CGAATTCTTAGCCAGAAATAATCGACAAGTCATTTC mGPR120_F01:
                                    (SEQ ID NO: 3)
AGGATCCGCCGCCATGTCCCCTGAGTGTGCACAGACGAC mGPR120_R01:
                                    (SEQ ID NO: 4)
CGAATTCTTAGCTGGAAATAACAGACAAGTCATTTC
```

As samples for PCR, human small intestine Marathon-ready cDNA (CLONTECH, current corporate name: TaKaRa) and cDMA obtained by reverse transcription of mouse BAT-derived RNA were used for human and mouse GPR120 receptor genes, respectively.

Using KOD Plus (TOYOBO) for PCR, 30 cycles of 94° C. for 2 minutes, 94° C. for 15 seconds, 55° C. for 30 seconds and 68° C. for 1 minute were carried out to effect reaction, followed by addition of 0.5 units of ExTaq (TaKaRa) and incubation at 72° C. for 10 minutes to carry out A-addition reaction to terminals. For mouse PCR, 35 cycles were carried out on the condition of a final DMSO concentration of 2%.

Cloning of amplified PCR products was carried out using pCR2.1-TOPO TA cloning kit (Invitrogen). For verification of base sequences, electrophoresis was carried out using Big-Dye Terminator Cycle Sequencing Ready Reaction Kit Ver. 3.0 and 377 DNA Sequencer (Applied Biosystems) to determine the base sequences. The human GPR120 gene was 16 amino acids shorter than the sequence registered as GenBank Accession NO. NM 181745.

The GPR120 receptor genes cloned into pCR2.1-TOPO vectors, into which the restriction enzymes, BamHI and EcoRI, recognition sites were introduced, were excised from the vectors by the enzymes and subcloned into the BamHI and EcoRI recognition sites of eucaryotic expression vector EF1/V5-His B (Invitrogen).

Test 2: Production of Expression Cells

Using Lipofectamine 2000 (Invitrogen), cDNA of GPR120 receptor was transfected into CHO/NFAT-BLA cells, and drug-resistant cells were isolated to obtain GPR120 stable expression strains. The GPR120-expressed CHO cells were cultured in DMEM/F12 medium containing 10% fetal bovine serum, 100 units/ml penicillin, 0.1 mg/ml streptomycin sulfate, 250 µg/ml Zeocin, 500 µg/mL Geneticin and 15 mM HEPES.

Test 3: Measurement of Intracellular Calcium Concentration

On the day before the measurement day, 4 µM Fluo-4 AM (fluorescence calcium indicator reagent) was incubated to be introduced into the human GPR120 expression CHO cells plated at 20000 cells per well of a 96-well black plate (ViewPlate; Packard) in the presence of 2.5 mM probenecid in a $CO_2$ incubator for 1 hour. To the cells was added the test compound diluted with HBSS solution containing 20 mM HEPES and 2.5 mM probenecid. Variations in the intracellular calcium concentration were measured by Fluorescence Imaging Plate Reader (FLIPR; Molecular Devices) to examine the agonist action, and $EC_{50}$ values were calculated.

The GPR120 agonist action of the compound groups encompassed by the compound according to an embodiment of the present invention is as follows.

TABLE 5

| Compound of Example | EC50 (µM) |
| --- | --- |
| Example 1 | 0.85 |
| Example 2 | 0.18 |

The above results exhibit that a compound according to an embodiment of the present invention or a pharmaceutically acceptable salt thereof has a GPR120 agonist action and is useful for treating and/or preventing diabetes, obesity and hyperlipidemia.

The invention claimed is:

1. A compound represented by a formula (I):

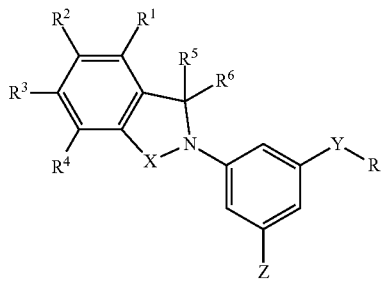

or a pharmaceutically acceptable salt thereof, wherein:
$R^1$, $R^2$, $R^3$ and $R^4$ each independently represent a hydrogen or halogen atom;
$R^5$ and $R^6$ each independently represent a hydrogen atom or lower alkyl or together represent oxo;
X represents $S(O)_2$;
Y represents an oxygen or sulfur atom, NH or $CH_2$;
Z represents a hydrogen or halogen atom;
R represents
(1) 5- or 6-membered heteroaryl having 1-3 hetero atoms selected from the group consisting of nitrogen, sulfur and oxygen atoms, contained within a ring,
said 5- or 6-membered heteroaryl is optionally substituted with 1 to 3 same or different lower alkyl, lower alkoxy or halogen atoms,
said lower alkyl and lower alkoxy is optionally substituted with 1 to 3 same or different halogen atoms, or
(2) $C_{3-7}$cycloalkyl substituted with oxo,
one of carbon atoms of said $C_{3-7}$cycloalkyl is optionally replaced by nitrogen atom, and
said $C_{3-7}$cycloalkyl in which one carbon atom is replaced by nitrogen atom is optionally substituted with 1 to 3, same or different lower alkyl, lower alkoxy or halogen atoms,
said lower alkyl and lower alkoxy is optionally substituted with 1 to 3 same or different halogen atoms.

2. The compound according to claim 1, or the pharmaceutically acceptable salt thereof, wherein Y is an oxygen atom or $CH_2$.

3. The compound according to claim 1, or the pharmaceutically acceptable salt thereof, wherein Y is an oxygen atom.

4. The compound according to claim 3, or the pharmaceutically acceptable salt thereof, wherein:
R is:
(1) a group selected from the group consisting of pyridinyl, pyrazinyl, pyrimidinyl, pyridazinyl, thiazolyl, thiadiazolyl, oxazolyl and pyrazolyl; or
(2) a group selected from the group consisting of cyclobutyl, cyclopentyl, cyclohexyl, cycloheptyl, pyrrolidinyl, piperidinyl and hexamethyleneiminyl groups, which are substituted with oxo and are optionally substituted with 1 to 3 same or different lower alkyl, lower alkoxy or halogen atoms,
said lower alkyl and lower alkoxy are optionally substituted with 1 to 3 same or different halogen atoms.

5. The compound according to claim 3, or the pharmaceutically acceptable salt thereof, wherein R is a group selected from the group consisting of pyridinyl, pyrazinyl, pyrimidinyl, pyridazinyl, thiazolyl, thiadiazolyl, oxazolyl and pyrazolyl.

6. The compound according to claim 3, or the pharmaceutically acceptable salt thereof, wherein R is a group selected from the group consisting of cyclobutyl, cyclopentyl, cyclohexyl, cycloheptyl, pyrrolidinyl, piperidinyl and hexamethyleneiminyl groups, which are substituted with oxo and are optionally substituted with 1 to 3 same or different lower alkyl, lower alkoxy or halogen atoms,
said lower alkyl and lower alkoxy are optionally substituted with 1 to 3 same or different halogen atoms.

7. The compound according to claim 1, or the pharmaceutically acceptable salt thereof, wherein formula (II):

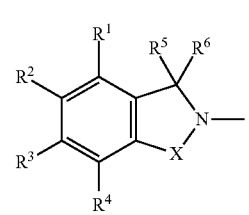

in the formula (I) is a group selected from the group consisting of formula (II-1):

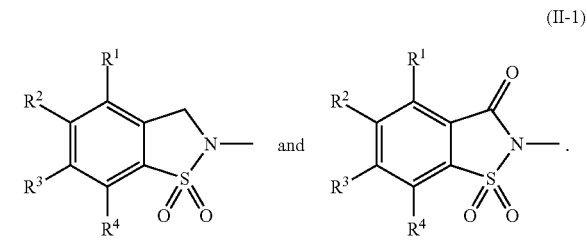

8. The compound according to claim 1, or the pharmaceutically acceptable salt thereof, wherein the formula (II) is a group selected from the group consisting of formula (II-2):

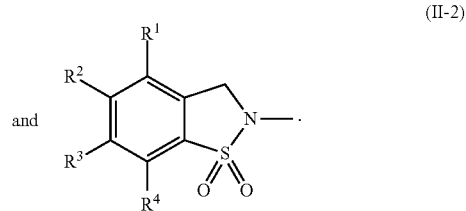

9. The compound according to claim 1, or the pharmaceutically acceptable salt thereof, wherein the compound represented by the formula (I) is
2-[3-fluoro-5-(pyridine-3-yloxy)phenyl]-2,3-dihydro-1,2-benzisothiazol-1,1-dioxide,
2-[3-fluoro-5-(pyrazin-2-yloxy)phenyl]-2,3-dihydro-1,2-benzisothiazol-1,1-dioxide,
2-[3-fluoro-(pyridine-3-yloxy)phenyl]-1,2-benzisothiazol-3(2H)-on-1,1-dioxide,
2-{3-fluoro-5-[(3-methylpyrazin-2-yl)oxy]phenyl}-2,3-dihydro-1,2-benzisothiazol-1,1-dioxide,
2-[3-fluoro-5-(pyrimidin-2-yloxy)phenyl]-2,3-dihydro-1,2-benzisothiazol-1,1-dioxide,
2-[3-fluoro-5-(1,3-thiazoyl-2-yloxy)phenyl]-2,3-dihydro-1,2-benzisothiazol-1,1-dioxide, 2-[3-fluoro-5-(pyrimidin-4-yloxy)phenyl]-2,3-dihydro-1,2-benzisothiazol-1,1-dioxide, 2-[3-(1,1-dioxide-1,2-benzisothiazol-2(3H)-yl)-5-fluorophenoxy]cyclohexanone, 2-[3-(1,1-dioxide-1,2-benzisothiazol-2(3H)-yl)-5-fluorophenoxy]cyclopentanone or 3-[3-(1,1-dioxide-1,2-benzisothiazol-2(3H)-yl)-5-fluorophenoxy]pyrrolidin-2-one.

10. A pharmaceutical composition comprising a compound of claim 1, or a pharmaceutically acceptable salt thereof, and a pharmaceutically acceptable carrier.

11. A method for treating diabetes mellitus, obesity or hyperlipidemia in a subject in need thereof which comprises administering to said subject a therapeutically effective amount of a compound of claim 1, or a pharmaceutically acceptable salt thereof.

* * * * *

SEQUENCE LISTING

<160> NUMBER OF SEQ ID NOS: 4

<210> SEQ ID NO 1
<211> LENGTH: 38
<212> TYPE: DNA
<213> ORGANISM: homo sapiens

<400> SEQUENCE: 1
aggatccgcc gccatgtccc ctgaatgcgc gcgggcag                38

<210> SEQ ID NO 2
<211> LENGTH: 36
<212> TYPE: DNA
<213> ORGANISM: homo sapiens

<400> SEQUENCE: 2
cgaattctta gccagaaata atcgacaagt catttc                36

<210> SEQ ID NO 3
<211> LENGTH: 39
<212> TYPE: DNA
<213> ORGANISM: mouse

<400> SEQUENCE: 3
aggatccgcc gccatgtccc ctgagtgtgc acagacgac                39

<210> SEQ ID NO 4
<211> LENGTH: 36
<212> TYPE: DNA
<213> ORGANISM: mouse

<400> SEQUENCE: 4
cgaattctta gctggaaata acagacaagt catttc                36